United States Patent [19]
Kim et al.

[11] Patent Number: 6,111,132
[45] Date of Patent: Aug. 29, 2000

[54] COMPOUNDS AND METHODS FOR SYNTHESIS AND THERAPY

[75] Inventors: Choung U. Kim, San Carlos; Willard Lew, San Mateo, both of Calif.

[73] Assignee: Gilead Sciences, Inc., Foster City, Calif.

[21] Appl. No.: 09/208,646

[22] Filed: Dec. 10, 1998

Related U.S. Application Data

[60] Provisional application No. 60/069,553, Dec. 12, 1997.

[51] Int. Cl.[7] .................................. C07C 205/00
[52] U.S. Cl. .......................... 560/125; 564/123
[58] Field of Search .............. 560/125; 564/123

[56] References Cited

U.S. PATENT DOCUMENTS

| | | | |
|---|---|---|---|
| 4,968,788 | 11/1990 | Farquhar | 536/27 |
| 5,175,273 | 12/1992 | Bischofberger et al. . | |
| 5,206,400 | 4/1993 | Witiak et al. . | |
| 5,292,938 | 3/1994 | Mease et al. . | |
| 5,360,817 | 11/1994 | von Izstein et al. | 514/459 |
| 5,428,073 | 6/1995 | Kunisch et al. . | |
| 5,512,596 | 4/1996 | Kim et al. | 514/568 |
| 5,514,798 | 5/1996 | Bischofberger et al. . | |
| 5,536,734 | 7/1996 | Mueller et al. | 514/336 |
| 5,556,963 | 9/1996 | Liav et al. . | |
| 5,597,933 | 1/1997 | Searle et al. . | |
| 5,602,277 | 2/1997 | Babu et al. . | |
| 5,622,916 | 4/1997 | Kunisch et al. . | |
| 5,633,360 | 5/1997 | Bischofberger et al. . | |
| 5,714,509 | 2/1998 | Luo et al. . | |
| 5,763,483 | 6/1998 | Bischofberger et al. | 514/529 |
| 5,866,601 | 2/1999 | Lew et al. | 514/459 |

FOREIGN PATENT DOCUMENTS

| | | |
|---|---|---|
| PJ 9800 | 11/1991 | Australia . |
| PK 2896 | 11/1991 | Australia . |
| PK 4537 | 11/1991 | Australia . |
| 654815 | 11/1994 | Australia . |
| 0 534 216 A1 | 9/1992 | European Pat. Off. . |
| 0 539 204 A1 | 10/1992 | European Pat. Off. . |
| 9510141 | 5/1995 | United Kingdom . |
| 9516276 | 8/1995 | United Kingdom . |
| 9525389 | 12/1995 | United Kingdom . |
| WO 91/16320 | 10/1991 | WIPO . |
| WO 92/06691 | 4/1992 | WIPO . |
| WO 93/12105 | 6/1993 | WIPO . |
| WO 93/16049 | 8/1993 | WIPO . |
| WO 94/07885 | 4/1994 | WIPO . |
| WO 94/07886 | 4/1994 | WIPO . |
| WO 94/28956 | 12/1994 | WIPO . |
| WO 94/29476 | 12/1994 | WIPO . |
| WO 95/00503 | 1/1995 | WIPO . |
| WO 95/16680 | 6/1995 | WIPO . |
| WO 95/18800 | 7/1995 | WIPO . |
| WO 95/20583 | 8/1995 | WIPO . |
| WO 95/32712 | 12/1995 | WIPO . |
| WO 96/04265 | 2/1996 | WIPO . |
| WO 96/14314 | 5/1996 | WIPO . |
| WO 96/26933 | 9/1996 | WIPO . |
| WO 96/30329 | 10/1996 | WIPO . |
| WO 96/34603 | 11/1996 | WIPO . |
| WO 96/36628 | 11/1996 | WIPO . |
| WO 96/39838 | 12/1996 | WIPO . |

OTHER PUBLICATIONS

Bamford et al., "Synthesis of 6–, 7– and 8–carbon sugar analogues of potent anti–influenza 2,3–didehydro–2, 3–dideoxy–N–acetylneuraminic acid derivatives", pp. 1181–1187, J Chem Soc Perkin Trans I, 1995.

Bamford, Mark J., "Neuraminidase Inhibitors as Potential Anti–Influenza Drugs", 10:1–16, J Enzyme Inhibition, 1995.

Burger, Alfred, "Relation of Chemical Structure and Biological Activity", Third edition, part 1, pp. 73–75, Medicinal Chemistry, 1979.

Carless et al., "Synthesis of Pseudo–alpha–L–fucopyranose from Toluene", pp. 2447–2448, J Chem Soc (C), 1995.

Chahoua et al., "Synthesis of (–)–Shikimate and (–)–Quinate 3–Phosphates by Differentiation of the Hydroxyl Functions of (–)–Shikimic and (–)–Quinic Acids", 57:5798–5801, J Org Chem, 1992.

Chandler et al., "Synthesis of the potent influenza neuraminidase inhibitor 4–quanidino Neu5Ac2en. X–Ray molecular structure of 5–acetamido–4–amino–2,6–anhydro–3,4,5–trideoxy–D–erythro–L–gluco–nononic acid", pp. 1173–1180, J Chem Soc Perkin Trans I, 1995.

Chandler et al., "Approaches to carbocyclic analogues of the potent neuraminidase inhibitor 4–guanidino–Neu5Ac2en. X–Ray molecular structure of N–[(1S,2S, 6R)–2–azido–6–benzyloxymethyl–4–formylcyclohex–3–enyl]acetamide", pp. 1189–1197, J Chem Soc Perkin Trans I, 1995.

Ciccotosto et al., "Synthesis of Methyl 5–Acetamido–3,4, 5–trideoxy–4–Guanidinyl–D–glycero–D–galacto–2– nonulopyranosidonic acid (4–deoxy–4–guanidino–Neu5Acalpha2Me)", 36(30):5405–5408, Tet Lett, 1995.

Colman, P.M., "Influenza virus neuraminidase: Structure, antibodies, and inhibitors", 3:1687–1696, Protein Science, 1994.

(List continued on next page.)

Primary Examiner—Gary Geist
Assistant Examiner—Taylor V Oh
Attorney, Agent, or Firm—Mark L. Bosse

[57] ABSTRACT

Novel compounds of Formula (I) are described.

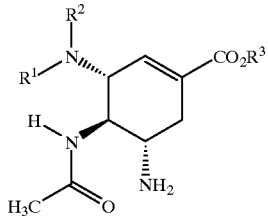

$R^1$, $R^2$, $R^3$, $R^4$, $R^5$ and $R^6$ are described in this specification.

Synthetic intermediates and pharmaceutical compositions comprising the inhibitors of the invention are also described. Methods of inhibiting neuraminidase in samples suspected of containing neuraminidase are also described. Assay methods for detecting neuraminidase activity are also described.

36 Claims, No Drawings

OTHER PUBLICATIONS

Dernick, Rudolf, "Sterical Requirements for Inhibitors of Viral Neuraminidases", 96:256, Chem Ab, 1982.

Douglas, R. Gordon, Jr., "Prophylaxis and Treatment of Influenza", 322(7):443–450, N Engl J Med, Feb. 15, 1990.

Fernandez et al., "New and Efficient Enantiospecific Synthesis of (–)-Methyl 5-epi-Shikimate and Methyl 5-epi-Quinate from (–)-Quinic Acid", 38(29):5225–5228, Tet Lett, 1997.

Funded Research Agreement, "Agreement between Gilead Sciences, Inc. and the University of California, Berkeley", 2 pages, , Dec. 7, 1995.

Ganem, Bruce, "Tetrahedron Report No. 59. From Glucose to Aromatics: Recent Developments in Natural Products of the Shikimic Acid Pathway", 34:3353–3383, Tetrahedron, 1978.

Grewe et al, "Eine einfache Synthese der Shikimisaure", 100:2546–2553, Chem Ber, 1967.

Grewe et al, "Synthese der Homochinasaure und des beta-Chino-athylamins", 575:1–17, Liebigs Ann Chem, 1952.

Grewe et al, "Darstellung und Eigenschaften des Chinaaldehyds", 658:113–119, Liebigs Ann Chem, 1962.

Grewe et al, "Uberfuhrung der Chinasaure in ungesattigte Verbindungen vom Typ der Shikimisaure", 69:61, Angew Chem Int Ed, 1957.

Grewe et al, "Die Uberfuhrung der Shikimisaure in Chinasaure", 86:928–938, Chem Ber, 1953.

Grewe et al, "Die Totalsynthese der Chinasaure", 87:793–802, Chem Ber, 1954.

Grewe et al, "Eine neue Synthese der Shikimisaure", 97:443–448, Chem Ber, 1964.

Grewe et al, "Abbau der Chinasaure nach Hunsdiecker", 98:104–110, Chem Ber, 1965.

Hanessian et al., "Anomeric Deoxygenation of 2-Ulosonic Acids Using SmI2: Rapid Access to 2-Deoxy-KDO and 2-Deoxy-NANA", pp. 863–864, Synlett, Oct. 1994.

Hayden et al., "Safety and Efficacy of the Neuraminidase Inhibitor GG167 in Experimental Human Influenza", 275(4):295–299, JAMA, Jan. 1996.

Janakiraman et al., "Structure of Influenza Virus Neuraminidase B/Lee/40 Complexed with Sialic Acid and a Dehydro Analog at 1.8-Angstrom Resolution: Implications for the Catalytic Mechanism", 33:8172–8179, Biochem, 1994.

Kiefel et al., "Synthesis and Biological Evaluation of N-Acetylneuraminic Acid-Based Rotavirus Inhibitors", 39:1314–1320, J Med Chem, 1996.

Kim et al., "Influenza Neuraminidase Inhibitors Possessing a Novel Hydrophobic Interaction in the Enzyme Active Site: Design, Synthesis, and Structural Analysis of Carbocyclic Sialic Acid Analogues with Potent Anti-Influenza Activity", 119:681–690, J Am Chem Soc, 1997.

Kong et al., "The First Synthesis of a C-7 Nitrogen-containing Sialic Acid Analogue, 5-Acetamido-7-azido-3,5,7-trideoxy-D-glycero-D-galacto-2-nonulopyranosonic acid (7-azido-7-deoxy-Neu5Ac)", 36(6):957–960, Tet Lett, 1995.

Kudo et al., "Synthesis of the Potent Inhibitors of Neuraminidase, N-(1,2-Dihydroxypropyl) Derivatives of Siastatin B and its 4-Deoxy Analogs", 46(2):300–309, J Antibiot, Feb. 1993.

Kudo, et al., "Syntheses and Activities of N-Substituted Derivatives of Siastatin B", 45(10):1662–1668, The Journal of Antibiotides, Oct. 1992.

Lew et al., "Carbocyclic Compounds", U.S. Patent Application No. 08/395,245, , Filed Feb. 27, 1995.

Luo et al., "Abstract of Presentation C52: Designed Non-Carbohydrate Inhibitors or Influenza Virus Neuraminidase and Accompanying Notes", , International Antiviral Conference, Nice, France, Jun. 10, 1994.

McCauley et al., "4-Guanidino-Neu5Ac2en fails to protect chickens from infection with highly pathogenic avian influenza virus", 27:179–186, Antiviral Res, 1995.

McKimm-Breschkin et al., "Generation and Characterization of Variants of NWS/G70C Influenza Virus after In Vitro Passage in 4-Amino-Neu5Ac2en and 4-Guanidino-Neu5Ac2en", 40(1):40–46, Antimicro Ag & Chemo, Jan. 1996.

Meindl et al., "2-Deoxy-2,3-dehydrosialic acids. 3. Inhibition of Vibrio cholerae[comma]neuraminidase by oxidation products of 2-deoxy-2,3-dehydro-N-acetylneuraminic acid", 73:42027b, Chem Ab, 1970.

Microbial Chem Res Found, "Siastatin B Derivative as Novel Antiviral Substance and its Production", Publication No. 04089481, Patent Abstracts of Japan, Mar. 23, 1992.

Nishimura et al., "Design of Potential Neuraminidase Inhibitors By Dehydration, Deoxygenation and Epimerization of Siastatin B", 1(1):39–44, Natural Product Letters, 1992.

Nishimura et al., "The First L-Iduronic Acid-Type 1-N-Iminosugars Having Inhibitory Activity of Experimental Metastasis", 118:3051–3052, J Am Chem Soc, 1996.

Nishimura et al., "Synthesis of 3-Episiastatin B Analogues Having Anti-Influenza Virus Activity", 46(12):1883–1889, J Antibiot, Dec. 1993.

Nishimura et al., "Totally Synthetic Analogues of Siastatin B. III. Trifluoroacetamide Analogues Having Inhibitory Activity for Tumor Metastasis", 47(1):101–107, The Journal of Antibiotics, Jan. 1994.

Nishimura, et al., "Potent Inhibition of Neuraminidase by N-(1,2-Dihydroxypropyl) Derivatives of Siastatin B and its Analogs", 1(1):33–38, Natural Product Letters, 1992.

Ogawa et al., "Synthesis of carbocyclic analogues of 3-deoxy-D-manno-2-octulosonic acid and N-acetylneuraminic acid", 269:53–78, Carb Res, 1995.

Ogawa et al., "Synthesis of a Carbocyclic Analogue of N-Acetylneuraminic Acid (Pseudo-N-acetylneuraminic Acid)", pp. 406–408, J Chem Soc (C), 1992.

Raner et al., "", 43:609–616, Aust J Chem, 1990.

Ryan et al., "Inhibition of Influenza Virus Replication in Mice by GG167 (4-Guanidino-2,4-Dideoxy-2,3-Dehydro-N-Acetylneuraminic Acid) Is Consistent with Extracellular Activity of Viral Neuraminidase (Sialidase)", 38(10:2270–2275, Antimicro Ag & Chemo, Oct. 1994.

Saito et al., "Steps in Maturation of Influenza A Virus Neuraminidase", 69(8):5011–5017, J Virol, Aug. 1995.

Singh et al., "Structure-Based Inhibitors of Influenza Virus Sialidase. A Benzoic Acid Lead with Novel Interaction", 38:3217–3225, J Med Chem, 1995.

Smith et al., "Synthesis and influenza virus sialidase inhibitory activity of analogues of 4-guanidino-Neu5Ac2en (GG167) with modified 5-substituents", 31:143–150, Eur J Med Chem, Jun. 22, 1995.

Smith et al., "Novel Inhibitors of Influenza Sialidases Related to GG167", 6(24):2931–2936, Bioorg Med Chem Lett, 1996.

Sollis et al, "Novel Inhibitors of Influenza Sialidase Related to GG167", 6(15):1805–1808, Abstract, Table of Contents, Bioorg Med Chem Lett, 1996.

Starkey et al., "Synthesis and Influenza Virus Sialidase Inhibitory Activity of the 5–Desacetamido Analogue of 2,3–Didehydro–2, 4–dideoxy–4–guanidinyl–N–acetylneuraminic acid", 36(2):299–302, Tet Lett, 1995.

Staschke et al., "Molecular Basis for the Resistance of Influenza Viruses to 4–Guanidino–Neu5Ac2en", 214:642–646, Virology, 1995.

Stevens, Ray, "Letter from Assistant Prof. Ray Stevens to Dr. Choung Kim", 1 page, , Oct. 10, 1996.

Stevens, Ray, "Letter from Assistant Prof. Ray Stevens to Dr. Choung Kim", 2 pages, , Feb. 18, 1996.

Ulibarri et al., "Construction of the Bicyclic Core Structure of the Enediyne Antibiotic Esperamicin–A1 in Either Enantiomeric Form from (–)–Quinic Acid", 60:2753–2761, J Org Chem, 1995.

Ulmer et al., "Heterologous Protection Against Influenza by Injection of DNA Encoding a Viral Protein", 259:1745–1749, Science, Mar. 19, 1993.

Wu et al., "Non–Sialate Inhibitor of Influenza A/WSN/33 Neuraminidase", 34:7154–7160, Biochem, 1995.

von Itzstein et al, "Rational design of potent sialidase–based inhibitors of influenza virus replication", 363:418–423, Nature, 1993.

von Itzstein et al., "A Study of the Active Site of Influenza Virus Sialidase: An Approach to the Rational Design of Novel Anti–influenza Drugs", 39:388–391, J Med Chem, 1996.

COMPOUNDS AND METHODS FOR SYNTHESIS AND THERAPY

This application claims the benefit of U.S. Provisional Application No. 60/069,553 filed Dec. 12, 1997.

BACKGROUND OF THE INVENTION

1. Field of the Invention

Neuraminidase (also known as sialidase, acylneuraminyl hydrolase, and EC 3.2.1.18) is an enzyme common among animals and a number of microorganisms. It is a glycohydrolase that cleaves terminal alpha-ketosidically linked sialic acids from glycoproteins, glycolipids and oligiosaccharides. Many of the microorganisms containing neuraminidase are pathogenic to man and other animals including fowl, horses, swine and seals. These pathogenic organisms include influenza virus.

Neuraminidase has been implicated in the pathogenicity of influenza viruses. It is thought to help the elution of newly synthesized virons from infected cells and assist in the movement of the virus (through its hydrolase activity) through the mucus of the respiratory tract.

2. Brief Description of Related Art von Itzstein, M. et al.; "Nature", 363(6428):418–423 (1993), discloses the rational design of sialidase-based inhibitors of influenza virus replication.

Colman, P. M. et al.; International Patent Publication No. WO 92/06691 (Int. App. No. PCT/AU90/00501, publication date Apr. 30, 1992), Itzstein, L. M. von et al.; European Patent Publication No. 0 539 204 Al (EP App. No. 92309684.6, publication date Apr. 28, 1993), and von Itzstein, M. et al.; International Publication No. WO 91/16320 (Int. App. No. PCT/AU91/00161, publication date Oct. 31, 1991) disclose compounds that bind neuraminidase and are asserted to exhibited antiviral activity in vivo.

Bischofberger, N. et al.; International Patent Publication No. WO 96/26933 (publication date Sep. 6, 1996) and copending U.S. Ser. No. 08/606,624 describe novel selective inhibitors of viral or bacterial neuraminidases.

OBJECTS OF THE INVENTION

A principal object of the invention is inhibition of viruses, in particular influenza viruses. In particular, an object is inhibition of glycolytic enzymes such as neuraminidase, in particular the selective inhibition of viral or bacterial neuraminidases.

An additional object of the invention is to provide neuraminidase inhibitors that have a retarded rate of urinary excretion, that enter into nasal or pulmonary secretions from the systemic circulation, that have sufficient oral bioavailability to be therapeutically effective, that possess elevated potency, that exhibit clinically acceptable toxicity profiles and have other desirable pharmacologic properties.

These and other objects will be readily apparent to the ordinary artisan from consideration of the invention as a whole.

SUMMARY OF THE INVENTION

The present invention is directed to compounds of the formula (I):

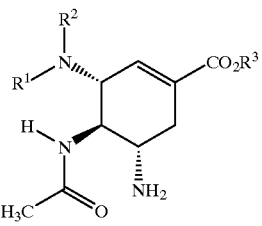

wherein:

$R^1$ is H, $R^2$ is —CH(CH$_2$CH$_3$)$_2$ and $R^3$ is H;
$R^1$ is H, $R^2$ is —CH(CH$_2$CH$_3$)$_2$ and $R^3$ is —CH$_2$CH$_3$;
$R^1$ is H, $R^2$ is —CH$_2$CH$_2$CH$_3$ and $R^3$ is H;
$R^1$ is H, $R^2$ is —CH$_2$CH$_2$CH$_3$ and $R^3$ is —CH$_2$CH$_3$;
$R^1$ is —CH$_3$, $R^2$ is —CH$_2$CH$_2$CH$_3$ and $R^3$ is H;
$R^1$ is —CH$_3$, $R^2$ is —CH$_2$CH$_2$CH$_3$ and $R^3$ is —CH$_2$CH$_3$;
$R^1$ is —CH$_3$, $R^2$ is —CH$_2$CH$_2$CH$_2$CH$_3$ and $R^3$ is H;
$R^1$ is —CH$_3$, $R^2$ is —CH$_2$CH$_2$CH$_2$CH$_3$ and $R^3$ is —CH$_2$CH$_3$;
$R^1$ is —CH$_3$, $R^2$ is —CH(CH$_2$CH$_3$)$_2$ and $R^3$ is H;
$R^1$ is —CH$_3$, $R^2$ is —CH(CH$_2$CH$_3$)$_2$ and $R^3$ is —CH$_2$CH$_3$;
$R^1$ is —CH$_3$, $R^2$ is —CH$_2$CH(CH$_2$CH$_3$)$_2$ and $R^3$ is H;
$R^1$ is —CH$_3$, $R^2$ is —CH$_2$CH(CH$_2$CH$_3$)$_2$ and $R^3$ is —CH$_2$CH$_3$;
$R^1$ is —CH$_3$, $R^2$ is —CH$_2$CH$_2$Ph and $R^3$ is H;
$R^1$ is —CH$_3$, $R^2$ is —CH$_2$CH$_2$Ph and $R^3$ is —CH$_2$CH$_3$;
$R^1$ is —CH$_3$, $R^2$ is -(cyclohexyl) and $R^3$ is H;
$R^1$ is —CH$_3$, $R^2$ is -(cyclohexyl) and $R^3$ is —CH$_2$CH$_3$;
$R^1$ is —CH$_2$CH$_3$, $R^2$ is —CH$_2$CH$_2$CH$_3$ and $R^3$ is H;
$R^1$ is —CH$_2$CH$_3$, $R^2$ is —CH$_2$CH$_2$CH$_3$ and $R^3$ is —CH$_2$CH$_3$;
$R^1$ is —CH$_2$CH$_3$, $R^2$ is —CH$_2$CH$_2$CH$_2$CH$_3$ and $R^3$ is H;
$R^1$ is —CH$_2$CH$_3$, $R^2$ is —CH$_2$CH$_2$CH$_2$CH$_3$ and $R^3$ is —CH$_2$CH$_3$;
$R^1$ is —CH$_2$CH$_2$CH$_3$, $R^2$ is —CH$_2$CH$_2$CH$_3$ and $R^3$ is H;
$R^1$ is —CH$_2$CH$_2$CH$_3$, $R^2$ is —CH$_2$CH$_2$CH$_3$ and $R^3$ is —CH$_2$CH$_3$;
$R^1$ is —CH$_2$CH$_2$CH$_3$, $R^2$ is —CH2(cyclopropyl) and $R^3$ is H;
$R^1$ is —CH$_2$CH$_2$CH$_3$, $R^2$ is —CH2(cyclopropyl) and $R^3$ is —CH$_2$CH$_3$;
$R^1$ and $R^2$ are taken together to form —CH$_2$CH$_2$CH$_2$CH$_2$— and $R^3$ is H;
$R^1$ and $R^2$ are taken together to form —CH$_2$CH$_2$CH$_2$CH$_2$— and $R^3$ is —CH$_2$CH$_3$;
$R^1$ and $R^2$ are taken together to form —CH$_2$CH$_2$CH$_2$CH$_2$CH$_2$— and $R^3$ is H;
$R^1$ and $R^2$ are taken together to form —CH$_2$CH$_2$CH$_2$CH$_2$CH$_2$— and $R^3$ is —CH$_2$CH$_3$;
$R^1$ and $R^2$ are taken together to form —CH$_2$CH$_2$OCH$_2$CH$_2$— and $R^3$ is H; or
$R^1$ and $R^2$ are taken together to form —CH$_2$CH$_2$OCH$_2$CH$_2$— and $R^3$ is —CH$_2$CH$_3$;
and salts, solvates and resolved enantiomers thereof.

The present invention is also directed to compounds of the formula (II):

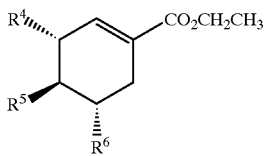

II wherein:

R⁴ is —OH, R⁵ is —NH₂ and R⁶ is —N₃;

R⁴ is —OC(O)CH₃, R⁵ is —N(H)(C(O)CH₃) and R⁶ is —N₃;

R⁴ is —N(CH₃)(CH₂CH₂CH₃), —N(CH₃)(CH₂CH₂CH₂CH₃), —N(CH₃)(CH(CH₂CH₃)₂), —N(CH₃)(CH₂CH(CH₂CH₃)₂), —N(CH₃)(CH₂CH₂Ph), —N(CH₃)(cyclohexyl), —N(CH₂CH₃)(CH₂CH₂CH₃), —N(CH₂CH₃)(CH₂CH₂CH₂CH₃), —N(CH₂CH₂CH₃)(CH₂CH₂CH₃), —N(CH₂CH₂CH₃)(CH₂(cyclopropyl), -(1-C₄H₈N), -(1-C₅H₁₀N), or -(1-C₄H₈NO);

R⁵ is —N(H)(C(O)CH₃) and R⁶ is —N₃;

R⁴ is —N(CH₃)(CH₂CH₂CH₃), —N(CH₃)(CH₂CH₂CH₂CH₃), —N(CH₃)(CH(CH₂CH₃)₂), —N(CH₃)(CH₂CH(CH₂CH₃)₂), —N(CH₃)(CH₂CH₂Ph), —N(CH₃)(cyclohexyl), —N(CH₂CH₃)(CH₂CH₂CH₃), —N(CH₂CH₃)(CH₂CH₂CH₂CH₃), —N(CH₂CH₂CH₃)(CH₂CH₂CH₃), —N(CH₂CH₂CH₃)(CH₂(cyclopropyl), -(1-C₄H₈N), -(1-C₅H₁₀N), or -(1-C₄H₈NO);

R⁵ is —N(H)(C(O)CH₃) and R⁶ is —NH₂;

R⁴ is —OC(O)CH₃, R⁵ is —N(H)(C(O)CH₃) and R⁶ is —NH₂;

R⁴ is —OC(O)CH₃, R⁵ is —N(H)(C(O)CH₃) and R⁶ is —N(H)(C(O)OC(CH₃)₃);

R⁴ is —N₃, R⁵ is —N(H)(C(O)CH₃) and R⁶ is —N(H)(C(O)OC(CH₃)₃);

R⁴ is —NH₂, R⁵ is —N(H)(C(O)CH₃) and R⁶ is —N(H)(C(O)OC(CH₃)₃);

R⁴ is —N(H)(CH₂CH₂CH₃), or —N(H)(CH(CH₂CH₃)₂), R⁵ is —N(H)(C(O)CH₃) and R⁶ is —N(H)(C(O)OC(CH₃)₃);

R⁴ is —N(H)(CH₂CH₂CH₃), or —N(H)(CH(CH₂CH₃)₂), R⁵ is —N(H)(C(O)CH₃) and R⁶ is —NH₂; or R⁴ is —OCH₂OCH₃, R⁵ is —NH₂ and R⁶ is —N₃;

and salts, solvates and resolved enantiomers thereof.

The present invention is also directed to compounds of the formula (III):

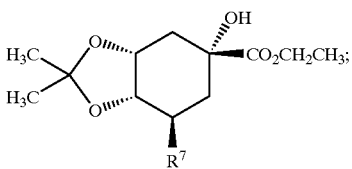

III wherein:

R⁷ is —OH or —OMs;

and salts, solvates and resolved enantiomers thereof.

The present invention is also directed to compounds of the formula (IV):

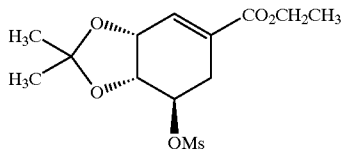

IV and salts, solvates and resolved enantiomers thereof.

The present invention is also directed to compounds of the formula (V):

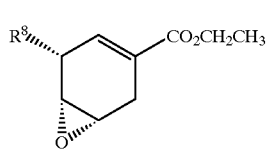

V wherein:

R⁸ is —OH, or —OCH₂OCH₃;

and salts, solvates and resolved enantiomers thereof.

The present invention is also directed to compounds of the formula (VI):

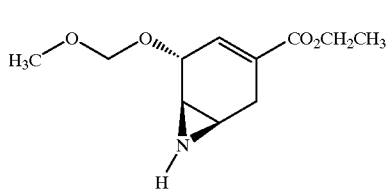

VI and salts, solvates and resolved enantiomers thereof.

The present invention is also directed to compounds of the formula (VII):

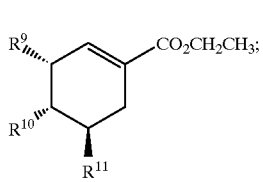

VII wherein:

R⁹ is —OH, R₁₀ is —OH, and R₁₁ is —OMs;

R⁹ is —OCH₂OCH₃, R₁₀ is —OH, and R₁₁ is —N₃; or

R⁹ is —OCH₂OCH₃, R₁₀ is —OMs, and R₁₁ is —N₃;

and salts, solvates and resolved enantiomers thereof.

DETAILED DESCRIPTION

Compositions of the Invention

The compositions of the invention are described above in the Summary of the Invention.

"Ph" means phenyl (—C₆H₅), so that, for example, "—CH₂CH₂Ph" means a group of the form:

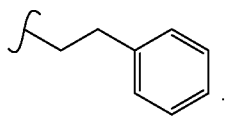

"Cyclohexyl" means a cyclohexane ring substituent (—$C_6H_{11}$), so that, for example, "-(cyclohexyl)" means a group of the form:

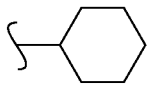

"Cyclopropyl" means a cyclopropane ring substituent (—$C_3H_5$), so that, for example, "—$CH_2$(cyclopropyl)" means a group of the form:

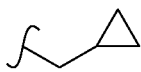

"$R^1$ and $R^2$ are taken together to form —$CH_2CH_2CH_2CH_2$—" means that $R^1$ and $R^2$ are combined to form a divalent substituent bonded to the nitrogen atom, so that, for example, a compound of Formula (I) wherein $R^1$ and $R^2$ are taken together to form —$CH_2CH_2CH_2CH_2$— and $R^3$ is —$CH_2CH_3$; means a compound having the formula:

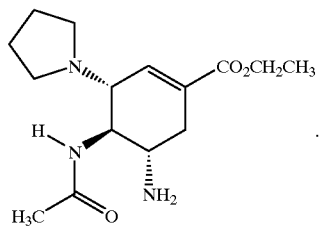

Similarly, a compound of formula (I) wherein $R^1$ and $R^2$ are taken together to form —$CH_2CH_2CH_2CH_2CH_2$— and $R^3$ is H; means a compound having the formula:

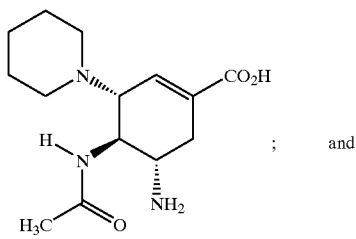

; and a compound of formula (I) wherein $R^1$ and $R^2$ are taken together to form —$CH_2CH_2OCH_2CH_2$— and $R^3$ is —$CH_2CH_3$; means a compound having the formula:

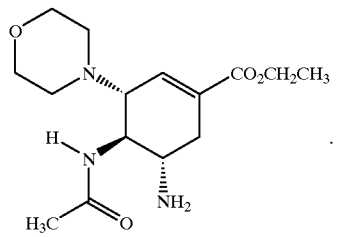

A substituent "-(1-$C_4H_8NO$)" is a group of the formula:

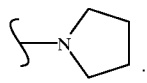

A substituent "-(1-$C_5H_{10}N$)" is a group of the formula:

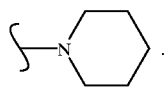

A substituent "-(1-$C_4H_8NO$)" is a group of the formula:

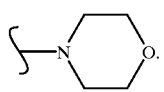

A substituent "—N(H)(C(O)$CH_3$)" is a group of the formula:

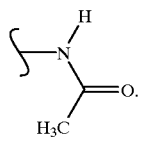

A substituent "—N(H)(C(O)OC($CH_3$)$_3$" is a group of the formula:

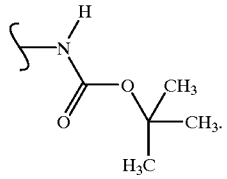

A substituent "—OMs" is a group of the formula:

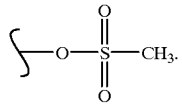

Salts and Hydrates

The compositions of this invention optionally comprise salts of the compounds herein, especially pharmaceutically acceptable non-toxic salts containing, for example, $Na^+$, $Li^+$, $K^+$, $Ca^{++}$ and $Mg^{++}$. Such salts may include those derived by combination of appropriate cations such as alkali and alkaline earth metal ions or ammonium and quaternary amino ions with the carboxylic acid. Monovalent salts are preferred if a water soluble salt is desired.

Metal salts typically are prepared by reacting the metal hydroxide with a compound of this invention. Examples of metal salts which are prepared in this way are salts containing $Li^+$, $Na^+$, and $K^+$. A less soluble metal salt can be precipitated from the solution of a more soluble salt by addition of the suitable metal compound.

In addition, salts may be formed from acid addition of certain organic and inorganic acids, e.g., HCl, HBr, $H_2SO_4$, $H_3PO_4$, or organic sulfonic acids, to basic centers, typically the amine. Finally, it is to be understood that the compositions herein comprise compounds of the invention in their unionized, as well as zwitterionic form, and combinations with stoichiometric amounts of water as in hydrates.

Also included within the scope of this invention are the salts of the parental compounds with one or more amino acids. Any amino acids are suitable, especially the naturally-occurring amino acids found as protein components, although the amino acid typically is one bearing a side chain with a basic or acidic group, e.g., lysine, arginine or glutamic acid, or a neutral group such as glycine, serine, threonine, alanine, isoleucine, or leucine.

Methods of Inhibition of Neuraminidase

Another aspect of the invention relates to methods of inhibiting the activity of neuraminidase comprising the step of treating a sample suspected of containing neuraminidase with a compound of the invention.

Compositions of the invention act as inhibitors of neuraminidase or as intermediates for such inhibitors. The inhibitors will bind to locations on the surface or in a cavity of neuraminidase having a geometry unique to neuraminidase. Compositions binding neuraminidase may bind with varying degrees of reversibility. Those compounds binding substantially irreversibly are ideal candidates for use in this method of the invention. In a typical embodiment the compositions bind neuraminidase with a binding coefficient of less than $10^{-4}M$, more typically less than $10^{-6}M$, still more typically $10^{-8}M$.

Within the context of the invention samples suspected of containing neuraminidase include natural or man-made materials such as living organisms; tissue or cell cultures; biological samples such as biological material samples (blood, serum, urine, cerebrospinal fluid, tears, sputum, saliva, tissue samples, and the like); laboratory samples; food, water, or air samples; bioproduct samples such as extracts of cells, particularly recombinant cells synthesizing a desired glycoprotein; and the like. Typically the sample will be suspected of containing an organism which produces neuraminidase, frequently a pathogenic organism such as a virus. Samples can be contained in any medium including water and organic solvent/water mixtures. Samples include living organisms such as humans, and man made materials such as cell cultures.

The treating step of the invention comprises adding the composition of the invention to the sample or it comprises adding a precursor of the composition to the sample. The addition step comprises any method of administration as described above.

If desired, the activity of neuraminidase after application of the composition can be observed by any method including direct and indirect methods of detecting neuraminidase activity. Quantitative, qualitative, and semiquantitative methods of determining neuraminidase activity are all contemplated. Typically one of the screening methods described above is applied. However, any other method is applicable, such as observation of the physiological properties of a living organism.

Organisms that contain neuraminidase include bacteria (*Vibrio cholerae, Clostridium perfringens, Streptococcus pneumoniae,* and *Arthrobacter sialophilus*) and viruses (especially orthomyxoviruses or paramyxoviruses such as influenza virus A and B, parainfluenza virus, mumps virus, Newcastle disease virus, fowl plague virus, and sendai virus). Inhibition of neuraminidase activity obtained from or found within any of these organisms is within the objects of this invention. The virology of influenza viruses is described in "Fundamental Virology" (Raven Press, New York, 1986), Chapter 24. The compounds of this invention are useful in the treatment or prophylaxis of such infections in animals, e.g. duck, rodents, or swine, or in man.

Screens for Neuraminidase Inhibitors

Compositions of the invention are screened for inhibitory activity against neuraminidase by any of the conventional techniques for evaluating enzyme activity. Within the context of the invention, typically compositions are first screened for inhibition of neuraminidase in vitro and compositions showing inhibitory activity are then screened for activity in vivo. Compositions having in vitro Ki (inhibitory constants) of less then about $5 \times 10^{-6}$ M, typically less than about $1 \times 10^{-7}$ M and preferably less than about $5 \times 10^{-8}$ M are preferred for in vivo use.

Useful in vitro screens have been described in detail and will not be elaborated here. However, von Itzstein, M. et al.; "Nature", 363(6428):418–423 (1993), in particular page 420, column 2, full paragraph 3, to page 421, column 2, first partial paragraph, describes a suitable in vitro assay of Potier, M.; et al.; "Analyt. Biochem.", 94:287–296 (1979), as modified by Chong, A. K. J.; et al.; "Biochem. Biophys. Acta", 1077:65–71 (1991); and Colman, P. M.; et al.; International Publication No. WO 92/06691 (Int. App. No. PCT/AU90/00501, publication date Apr. 30, 1992) page 34, line 13, to page 35, line 16, describes another useful in vitro screen.

In vivo screens have also been described in detail. See von Itzstein, M. et al.; op. cit., in particular page 421, column 2, first full paragraph, to page 423, column 2, first partial paragraph, and Colman, P. M.; et al.; op. cit. page 36, lines 1–38.

Pharmaceutical Formulations and Routes of Administration

The compounds of this invention are formulated with conventional carriers and excipients, which will be selected in accord with ordinary practice. Tablets will contain excipients, glidants, fillers, binders and the like. Aqueous formulations are prepared in sterile form, and when intended for delivery by other than oral administration generally will be isotonic. All formulations will optionally contain excipients such as those set forth in the "Handbook of Pharmaceutical Excipients" (1986). Excipients include ascorbic acid and other antioxidants, chelating agents such as EDTA, carbohydrates such as dextrin, hydroxyalkylcellulose, hydroxyalkylmethylcellulose, stearic acid and the like. The pH of the formulations ranges from about 3 to about 11, but is ordinarily about 7 to 10.

One or more compounds of the invention (herein referred to as the active ingredients) are administered by any route appropriate to the condition to be treated. Suitable routes include oral, rectal, nasal, topical (including buccal and sublingual), vaginal and parenteral (including subcutaneous, intramuscular, intravenous, intradermal, intrathecal and epidural), and the like. It will be appreciated that the preferred route may vary with for example the condition of the recipient. An advantage of the compounds of this invention is that they are orally bioavailable and can be dosed orally; it is not necessary to administer them by intrapulmonary or intranasal routes. Surprisingly, (in view of, inter alia Bamford, M. J., "J. Enzyme Inhibition" 10:1–6 (1995), and especially p. 15, first full paragraph), the anti-influenza compounds of WO 91/16320, WO 92/06691 and U.S. Pat. No. 5,360,817 are successfully administered by the oral or intraperitoneal routes. See Example 161 infra.

While it is possible for the active ingredients to be administered alone it may be preferable to present them as pharmaceutical formulations. The formulations, both for veterinary and for human use, of the invention comprise at least one active ingredient, as above defined, together with one or more acceptable carriers therefor and optionally other therapeutic ingredients. The carrier(s) must be "acceptable" in the sense of being compatible with the other ingredients of the formulation and physiologically innocuous to the recipient thereof.

The formulations include those suitable for the foregoing administration routes. The formulations may conveniently be presented in unit dosage form and may be prepared by any of the methods well known in the art of pharmacy. Techniques and formulations generally are found in Remington's Pharmaceutical Sciences (Mack Publishing Co., Easton, Pa.). Such methods include the step of bringing into association the active ingredient with the carrier which constitutes one or more accessory ingredients. In general the formulations are prepared by uniformly and intimately bringing into association the active ingredient with liquid carriers or finely divided solid carriers or both, and then, if necessary, shaping the product.

Formulations of the invention suitable for oral administration are prepared as discrete units such as capsules, cachets or tablets each containing a predetermined amount of the active ingredient; as a powder or granules; as solution or a suspension in an aqueous liquid or a non-aqueous liquid; or as an oil-in-water liquid emulsion or a water-in-oil liquid emulsion. The active ingredient may also be presented as a bolus, electuary or paste.

A tablet is made by compression or molding, optionally with one or more accessory ingredients. Compressed tablets may be prepared by compressing in a suitable machine the active ingredient in a free-flowing form such as a powder or granules, optionally mixed with a binder, lubricant, inert diluent, preservative, surface active or dispersing agent. Molded tablets may be made by molding in a suitable machine a mixture of the powdered active ingredient moistened with an inert liquid diluent. The tablets may optionally be coated or scored and optionally are formulated so as to provide slow or controlled release of the active ingredient therefrom. In one embodiment acid hydrolysis of the medicament is obviated by use of an enteric coating.

For infections of the eye or other external tissues e.g. mouth and skin, the formulations are preferably applied as a topical ointment or cream containing the active ingredient (s) in an amount of, for example, 0.075 to 20% w/w (including active ingredient(s) in a range between 0.1% and 20% in increments of 0.1% w/w such as 0.6% w/w, 0.7% w/w, etc.), preferably 0.2 to 15% w/w and most preferably 0.5 to 10% w/w. When formulated in an ointment, the active ingredients may be employed with either a paraffinic or a water-miscible ointment base. Alternatively, the active ingredients may be formulated in a cream with an oil-in-water cream base.

If desired, the aqueous phase of the cream base may include, for example, at least 30% w/w of a polyhydric alcohol, i.e. an alcohol having two or more hydroxyl groups such as propylene glycol, butane 1,3-diol, mannitol, sorbitol, glycerol and polyethylene glycol (including PEG 400) and mixtures thereof. The topical formulations may desirably include a compound which enhances absorption or penetration of the active ingredient through the skin or other affected areas. Examples of such dermal penetration enhancers include dimethyl sulphoxide and related analogs.

The oily phase of the emulsions of this invention may be constituted from known ingredients in a known manner. While the phase may comprise merely an emulsifier (otherwise known as an emulgent), it desirably comprises a mixture of at least one emulsifier with a fat or an oil or with both a fat and an oil. Preferably, a hydrophilic emulsifier is included together with a lipophilic emulsifier which acts as a stabilizer. It is also preferred to include both an oil and a fat. Together, the emulsifier(s) with or without stabilizer(s) make up the so-called emulsifying wax, and the wax together with the oil and fat make up the so-called emulsifying ointment base which forms the oily dispersed phase of the cream formulations.

Emulgents and emulsion stabilizers suitable for use in the formulation of the invention include Tween® 60, Span® 80, cetostearyl alcohol, benzyl alcohol, myristyl alcohol, glyceryl mono-stearate and sodium lauryl sulfate.

The choice of suitable oils or fats for the formulation is based on achieving the desired cosmetic properties. The cream should preferably be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters known as Crodamol CAP may be used, the last three being preferred esters. These may be used alone or in combination depending on the properties required. Alternatively, high melting point lipids such as white soft paraffin and/or liquid paraffin or other mineral oils are used.

Formulations suitable for topical administration to the eye also include eye drops wherein the active ingredient is dissolved or suspended in a suitable carrier, especially an aqueous solvent for the active ingredient. The active ingredient is preferably present in such formulations in a concentration of 0.5 to 20%, advantageously 0.5 to 10% particularly about 1.5% w/w.

Formulations suitable for topical administration in the mouth include lozenges comprising the active ingredient in a flavored basis, usually sucrose and acacia or tragacanth; pastilles comprising the active ingredient in an inert basis such as gelatin and glycerin, or sucrose and acacia; and mouthwashes comprising the active ingredient in a suitable liquid carrier.

Formulations for rectal administration may be presented as a suppository with a suitable base comprising for example cocoa butter or a salicylate.

Formulations suitable for intrapulmonary or nasal administration have a particle size for example in the range of 0.1 to 500 microns (including particle sizes in a range between 0.1 and 500 microns in increments microns such as 0.5, 1, 30 microns, 35 microns, etc.), which is administered by rapid inhalation through the nasal passage or by inhalation through the mouth so as to reach the alveolar sacs. Suitable formulations include aqueous or oily solutions of the active ingredient. Formulations suitable for aerosol or dry powder administration may be prepared according to conventional methods and may be delivered with other therapeutic agents such as compounds heretofore used in the treatment or prophylaxis of influenza A or B infections as described below.

Formulations suitable for vaginal administration may be presented as pessaries, tampons, creams, gels, pastes, foams or spray formulations containing in addition to the active ingredient such carriers as are known in the art to be appropriate.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents.

The formulations are presented in unit-dose or multi-dose containers, for example sealed ampoules and vials, and may be stored in a freeze-dried (lyophilized) condition requiring only the addition of the sterile liquid carrier, for example water for injection, immediately prior to use. Extemporaneous injection solutions and suspensions are prepared from sterile powders, granules and tablets of the kind previously described. Preferred unit dosage formulations are those containing a daily dose or unit daily sub-dose, as herein above recited, or an appropriate fraction thereof, of the active ingredient.

It should be understood that in addition to the ingredients particularly mentioned above the formulations of this invention may include other agents conventional in the art having regard to the type of formulation in question, for example those suitable for oral administration may include flavoring agents.

The invention further provides veterinary compositions comprising at least one active ingredient as above defined together with a veterinary carrier therefor.

Veterinary carriers are materials useful for the purpose of administering the composition and may be solid, liquid or gaseous materials which are otherwise inert or acceptable in the veterinary art and are compatible with the active ingredient. These veterinary compositions may be administered orally, parenterally or by any other desired route.

Compounds of the invention are used to provide controlled release pharmaceutical formulations containing as active ingredient one or more compounds of the invention ("controlled release formulations") in which the release of the compound is controlled and regulated to allow less frequency dosing or to improve the pharmacokinetic or toxicity profile of the compound.

The effective dose of compound depends at least on the nature of the condition being treated, toxicity, whether the compound is being used prophylactically (lower doses) or against an active influenza infection, the method of delivery, and the pharmaceutical formulation, and will be determined by the clinician using conventional dose escalation studies. It can be expected to be from about 0.0001 to about 100 mg/kg body weight per day. Typically, from about 0.01 to about 10 mg/kg body weight per day, usually from about 0.01 to about 5 mg/kg body weight per day, and more typically, from about 0.05 to about 0.5 mg/kg body weight per day. For example, the daily candidate dose for an adult human of approximately 70 kg body weight will range from 1 mg to 1000 mg, preferably between 5 mg and 500 mg, and may take the form of single or multiple doses.

Therapeutic compounds of the invention are also used in combination with other active ingredients. Such combinations are selected based on the condition to be treated, cross-reactivities of ingredients and pharmaco-properties of the combination. For example, when treating viral infections of the respiratory system, in particular influenza infection, the compositions of the invention are combined with antivirals (such as amantidine, rimantadine and ribavirin), mucolytics, expectorants, bronchodilators, antibiotics, antipyretics, or analgesics. Ordinarily, antibiotics, antipyretics, and analgesics are administered together with or in the same course of therapy with the compounds of this invention.

Metabolites of the Compounds of the Invention

Also falling within the scope of this invention are the in vivo metabolic products of the compounds described herein, to the extent such products are novel and unobvious over the prior art. Such products may result for example from the oxidation, reduction, hydrolysis, amidation, esterification and the like of the administered compound, primarily due to enzymatic processes. Accordingly, the invention includes novel and unobvious compounds produced by a process comprising contacting a compound of this invention with a mammal for a period of time sufficient to yield a metabolic product thereof. Such products typically are identified by preparing a radiolabelled (e.g. $C^{14}$ or $H^3$) compound of the invention, administering it parenterally in a detectable dose (e.g. greater than about 0.5 mg/kg) to an animal such as rat, mouse, guinea pig, monkey, or to man, allowing sufficient time for metabolism to occur (typically about 30 seconds to 30 hours) and isolating its conversion products from the urine, blood or other biological samples. These products are easily isolated since they are labeled (others are isolated by the use of antibodies capable of binding epitopes surviving in the metabolite). The metabolite structures are determined in conventional fashion, e.g. by MS or NMR analysis. In general, analysis of metabolites is done in the same way as conventional drug metabolism studies well-known to those skilled in the art. The conversion products, so long as they are not otherwise found in vivo, are useful in diagnostic assays for therapeutic dosing of the compounds of the invention even if they possess no neuraminidase inhibitory activity of their own.

Exemplary Methods of Making the Compounds of the Invention

The invention also relates to methods of making the compositions of the invention. The compositions are prepared by any of the applicable techniques of organic synthesis. Many such techniques are well known in the art. However, many of the known techniques are elaborated in "Compendium of Organic Synthetic Methods" (John Wiley & Sons, New York), Vol. 1, Ian T. Harrison and Shuyen Harrison, 1971; Vol. 2, Ian T. Harrison and Shuyen Harrison, 1974; Vol. 3, Louis S. Hegedus and Leroy Wade, 1977; Vol. 4, Leroy G. Wade, Jr., 1980; Vol. 5, Leroy G. Wade, Jr., 1984; and Vol. 6, Michael B. Smith; as well as March, J., "Advanced Organic Chemistry, Third Edition", Gohn Wiley & Sons, New York, 1985), "Comprehensive Organic Synthesis. Selectivity, Strategy & Efficiency in Modern Organic Chemistry. In 9 Volumes", Barry M. Trost, Editor-in-Chief (Pergamon Press, New York, 1993 printing).

A number of exemplary methods for the preparation of the compositions of the invention are provided below. These methods are intended to illustrate the nature of such preparations are not intended to limit the scope of applicable methods.

Generally, the reaction conditions such as temperature, reaction time, solvents, workup procedures, and the like, will be those common in the art for the particular reaction to be performed. The cited reference material, together with material cited therein, contains detailed descriptions of such conditions. Typically the temperatures will be −100° C. to 200° C., solvents will be aprotic or protic, and reaction times will be 10 seconds to 10 days. Workup typically consists of quenching any unreacted reagents followed by partition between a water/organic layer system (extraction) and separating the layer containing the product.

Oxidation and reduction reactions are typically carried out at temperatures near room temperature (about 20° C.), although for metal hydride reductions frequently the temperature is reduced to 0° C. to −100° C., solvents are typically aprotic for reductions and may be either protic or aprotic for oxidations. Reaction times are adjusted to achieve desired conversions.

Condensation reactions are typically carried out at temperatures near room temperature, although for non-equilibrating, kinetically controlled condensations reduced temperatures (0° C. to −100° C.) are also common. Solvents can be either protic (common in equilibrating reactions) or aprotic (common in kinetically controlled reactions).

Standard synthetic techniques such as azeotropic removal of reaction by-products and use of anhydrous reaction conditions (e.g. inert gas environments) are common in the art and will be applied when applicable.

Exemplary methods of preparing compounds of the invention are shown in Schemes 1–5 below. A detailed description of the methods are found in the Experimental section below.

Scheme 1

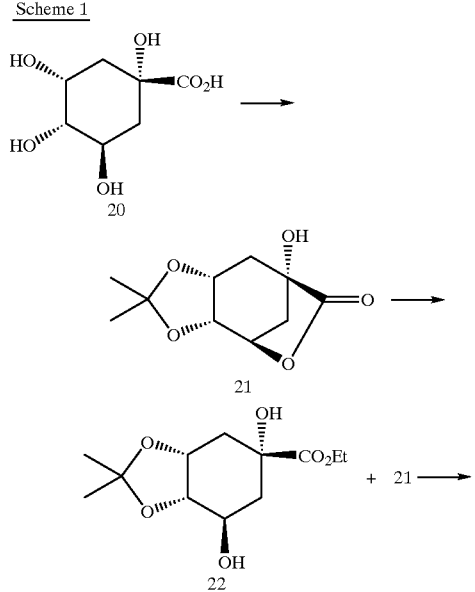

Scheme 2

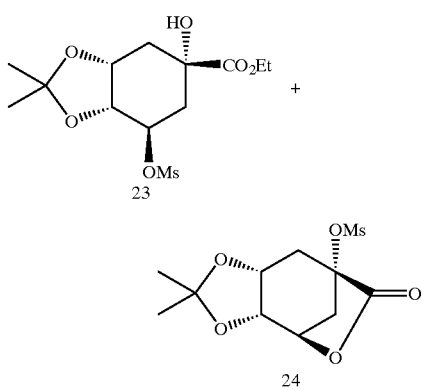

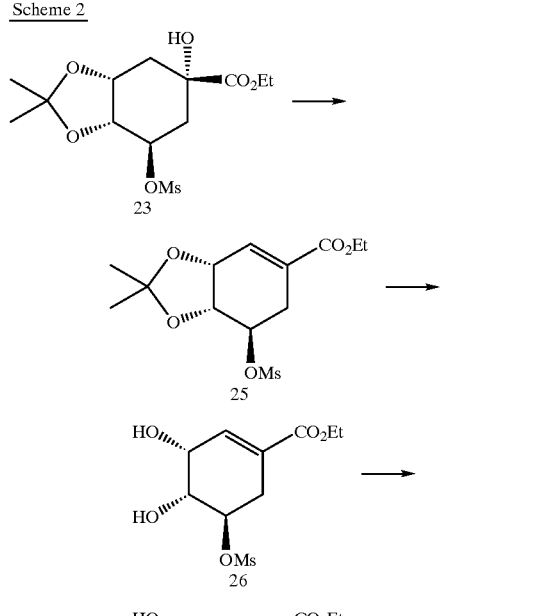

Scheme 3

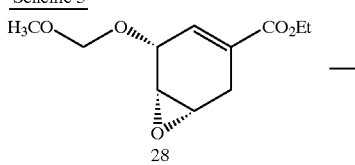

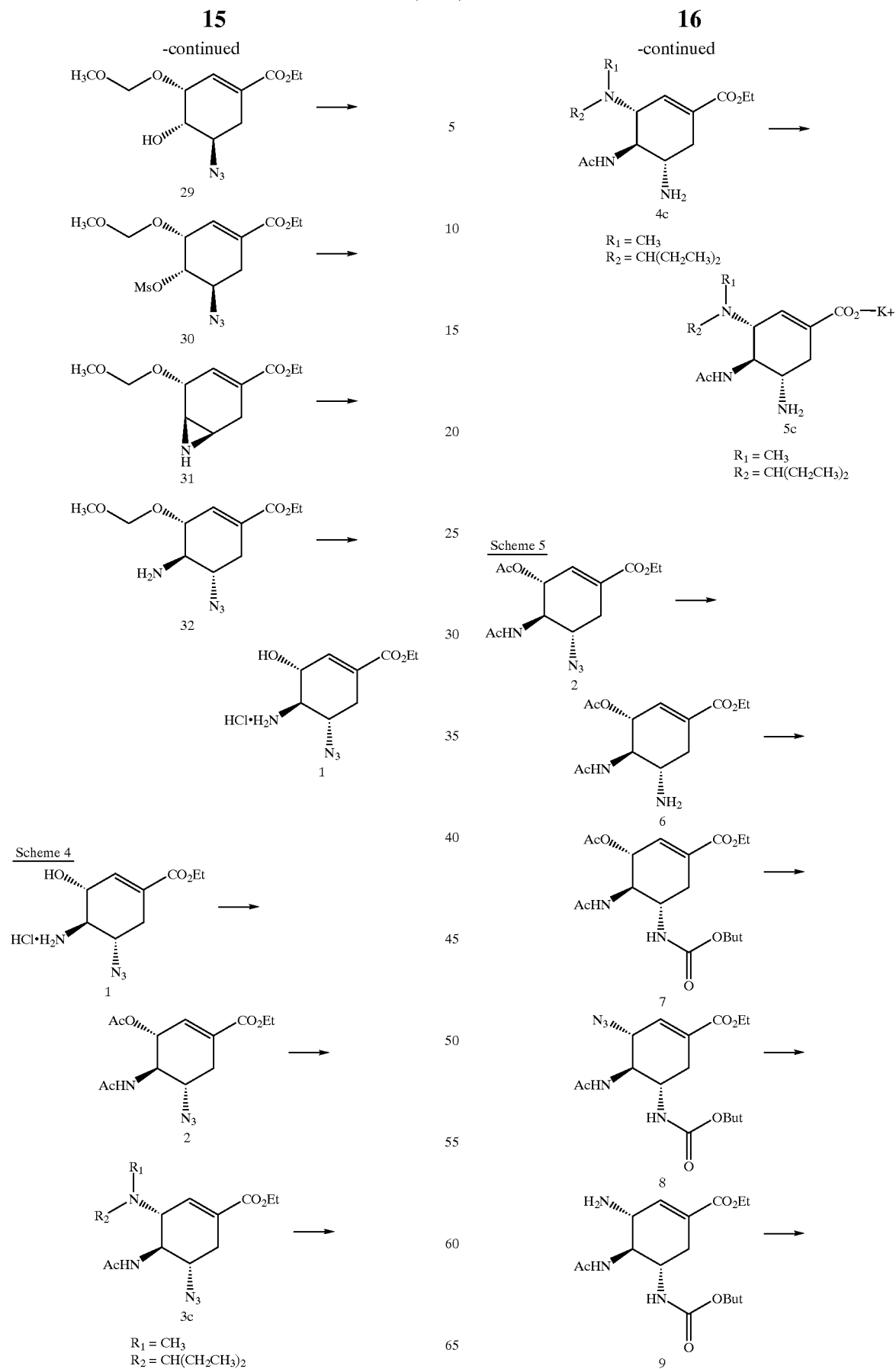

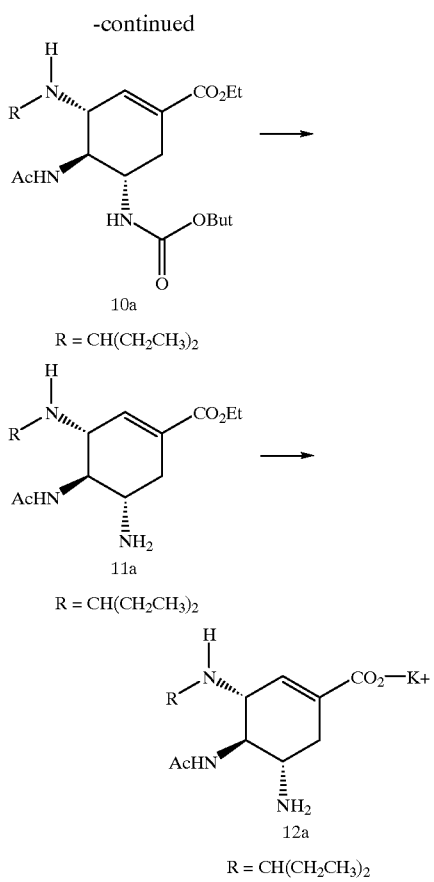

General aspects of these exemplary methods are described below and in the Examples. Each of the products of the following processes is optionally separated, isolated, and/or purified prior to its use in subsequent processes.

The terms "treated", "treating", "treatment", and the like, mean contacting, mixing, reacting, allowing to react, bringing into contact, and other terms common in the art for indicating that one or more chemical entities is treated in such a manner as to convert it to one or more other chemical entities. This means that "treating compound one with compound two" is synonymous with "allowing compound one to react with compound two", "contacting compound one with compound two", "reacting compound one with compound two", and other expressions common in the art of organic synthesis for reasonably indicating that compound one was "treated", "reacted", "allowed to react", etc., with compound two.

"Treating" indicates the reasonable and usual manner in which organic chemicals are allowed to react. Normal concentrations (0.01M to 10M, typically 0.1M to 1M), temperatures (−100° C. to 250° C., typically −78° C. to 150° C., more typically −78° C. to 100° C., still more typically 0° C. to 100° C.), reaction vessels (typically glass, plastic, metal), solvents, pressures, atmospheres (typically air for oxygen and water insensitive reactions or nitrogen or argon for oxygen or water sensitive), etc., are intended unless otherwise indicated. The knowledge of similar reactions known in the art of organic synthesis are used in selecting the conditions and apparatus for "treating" in a given process. In particular, one of ordinary skill in the art of organic synthesis selects conditions and apparatus reasonably expected to successfully carry out the chemical reactions of the described processes based on the knowledge in the art.

In each of the above exemplary schemes it may be advantageous to separate reaction products from one another and/or from starting materials. The desired products of each step or series of steps is separated and/or purified (hereinafter separated) to the desired degree of homogeneity by the techniques common in the art. Typically such separations involve multiphase extraction, crystallization from a solvent or solvent mixture, distillation, sublimation, or chromatography. Chromatography can involve any number of methods including, for example, size exclusion or ion exchange chromatography, high, medium, or low pressure liquid chromatography, small scale and preparative thin or thick layer chromatography, as well as techniques of small scale thin layer and flash chromatography.

Another class of separation methods involves treatment of a mixture with a reagent selected to bind to or render otherwise separable a desired product, unreacted starting material, reaction by product, or the like. Such reagents include adsorbents or absorbents such as activated carbon, molecular sieves, ion exchange media, or the like. Alternatively, the reagents can be acids in the case of a basic material, bases in the case of an acidic material, binding reagents such as antibodies, binding proteins, selective chelators such as crown ethers, liquid/liquid ion extraction reagents (LIX), or the like.

Selection of appropriate methods of separation depends on the nature of the materials involved. For example, boiling point, and molecular weight in distillation and sublimation, presence or absence of polar functional groups in chromatography, stability of materials in acidic and basic media in multiphase extraction, and the like. One skilled in the art will apply techniques most likely to achieve the desired separation.

All literature and patent citations above are hereby expressly incorporated by reference at the locations of their citation. Specifically cited sections or pages of the above cited works are incorporated by reference with specificity. The invention has been described in detail sufficient to allow one of ordinary skill in the art to make and use the subject matter of the following claims. It is apparent that certain modifications of the methods and compositions of the following claims can be made within the scope and spirit of the invention.

EXAMPLES

General

The following Examples refer to the Schemes.

Some Examples have been performed multiple times. In repeated Examples, reaction conditions such as time, temperature, concentration and the like, and yields were within normal experimental ranges. In repeated Examples where significant modifications were made, these have been noted where the results varied significantly from those described. In Examples where different starting materials were used, these are noted. When the repeated Examples refer to a "corresponding" analog of a compound, such as a "corresponding ethyl ester", this intends that an otherwise present group, in this case typically a methyl ester, is taken to be the same group modified as indicated. For example, the "corresponding acetate ester of compound 1" is Compound 2.

Example 1

Compound 21: To a solution of 20 (Quinic Acid, 300 g, 1.56 mole) in acetone (1.1 L) was added 2,2-dimethoxypropane (600 mL, 4.88 mole) and p-toluenesulfonic acid monohydrate (3.0 g, 15.8 mmol). The mixture was placed on a rotary evaporator at 60–65° C. at atmospheric pressure for 3 h. Solvents were evaporated and the residue was partitioned between ethyl acetate and water. The aqueous layer was extracted with ethyl acetate and the combined organic layers were washed with water, dried ($MgSO_4$), filtered and evaporated to give 21 (260 g, 78%) as a white solid.

Example 2

Compound 22: To a solution of 21 (259 g, 1.21 mole) in absolute ethanol (1.34 L ) was added 20% sodium ethoxide in ethanol (5.9 mL, 16 mmol). The solution was stirred at ambient temperature for 2 h. Acetic acid (1 mL, 18 mmol) was added and the solvents were distilled in vacuo. Ethyl acetate (600 mL) was added and the reaction was concentrated to near dryness. The solid residue was recrystallized from ethyl acetate/hexane to give an approximately 4.4:1 mixture of 22:21 (264 g, 84%) as a white crystalline solid which was used as is for the next reaction.

Example 3

Compound 23: To a solution of a mixture of 22 and 21 from the previous reaction (263 g, 1.01 mole) in dichloromethane (815 mL) cooled to –10 to 0° C. was added methanesulfonyl chloride (78 mL, 1.01 mole) and triethylamine (195 mL, 1.4 mole). An additional portion of methanesulfonyl chloride (8 mL, 0.10 mole) in dichloromethane (200 mL) was added. After 2 h at –10 to 0° C., another portion of methanesulfonyl chloride (5 mL, 0.06 mole) was added. After an additional 1 h at –10 to 0° C., water (140 mL) and 3% hydrochloric acid (154 mL) were added. The organic layer was washed with water and evaporated. The residue was dissolved in ethyl acetate and cooled to –10° to –20° C. for 2 h. After which compound 24 crystallized and was separated by filtration and washed with cold ethyl acetate. The filtrate was concentrated to give 23 (304 g, 89%) as an orange resin.

Example 4

Compound 25: To a solution of 23 (303 g, 0.895 mole) in pyridine (300 mL) and dicholomethane (1100 mL) cooled to –30 to –40° C. was added sulfuryl chloride (109 mL, 1.36 mole) dropwise. The mixture was stirred at –20 to –30° C. for 1 h followed by the dropwise addition of methanol (53 mL) at –30 to –40° C. The reaction mixture was allowed to warm to room temperature and stirred at ambient temperature overnight. Acetic acid (8 mL) was added followed by the addition of hexane (800 mL) and then filtered. The filtrate was evaporated and diluted with ethyl acetate. The organic layer was washed with water, dried ($MgSO_4$), filtered through a pad of silica gel and concentrated. The residue was precipitated from ethyl acetate and hexane to give 25 (189 g, 66%) as a red solid which contained ca. 20% of the corresponding olefin regioisomer.

Example 5

Compound 26: A mixture of 25 from the previous reaction (188 g, 0.587 mole) in ethanol (362 mL) was heated at 90–95° C. with the continuous removal of solvent via distillation over a 3.5 h period. The reaction mixture was concentrated to give a solid residue which was recrystallized from ethyl acetate and hexane to give 26 (99 g, 60%) as a white solid.

Example 6

Compound 27: To a solution of 26 (96.5 g, 0.344 mole) in anhydrous THF (750 mL) at 0° C. was added 1,8-Diazabicyclo [5.4.0]undec-7-ene (54 mL, 0.361 mole) dropwise. The mixture was stirred at 0° C. for 2 h and then at ambient temperature overnight. Acetic acid (1.2 g) was added and the reaction mixture was concentrated. The residue was dissolved in ethyl acetate/hexane (1/1) and filtered through a pad of silica gel. The filtrate was concentrated and precipitated from ethyl acetate and hexane to give 27 (58 g, 91%) as a white solid.

Example 7

Compound 28: To a solution of 27 (56.6 g, 0.307 mole) in dichloromethane (654 mL) were added N,N-Diisopropylethylamine (161 mL, 0.923 mole) and chloromethyl methyl ether (46.7 mL, 0.615 mole). The mixture was refluxed for 3 h, evaporated and partitioned between ethyl acetate and water. The aqueous layer was separated and extracted twice with ethyl acetate. The combined organic layer was washed with brine, dried ($MgSO_4$), filtered and evaporated to give 28 (70.2 g, 100%) as a yellow oil.

Example 8

Compound 29: To a solution of 28 (70.2 g, 0.307 mole) in ethanol (1.09 L) and water (218 mL) was added sodium azide (100 g, 1.54 mole) and ammonium chloride (36.2 g, 0.677 mole). The mixture was gently refluxed for 2 h followed by the addition of water (200 mL). Volatiles were removed under reduced pressure followed by extraction of the aqueous layer with ethyl acetate. The combined organic extracts were washed with brine, dried ($MgSO_4$), filtered and concentrated to give 29 (82 g, 98%) as a yellow oil.

Example 9

Compound 30: To a solution of 29 (81.7 g, 0.301 mole) in dichloromethane (690 mL) cooled to 0° C. was added triethylamine (58.8 mL, 0.422 mole) and methanesulfonyl chloride (28 mL, 0.362 mole). The solution was stirred at 0° C. for 2 h and then at ambient temperature for 30 min. Solvents were evaporated and the residue was partitioned between ethyl acetate and water. The aqueous layer was extracted twice with ethyl acetate, combined, washed with water, dried ($MgSO_4$), filtered and evaporated to give crude 30 (109 g) as a yellow oil.

Example 10

Compound 31: To a solution of crude 30 (109 g, 0.301 mole) in anhydrous THF (570 mL) cooled to 15–20° C. was added triphenylphosphine (86.9 g, 0.331 mole) in anhydrous THF (120 mL) dropwise. The mixture was stirred at ambient temperature for 4.5 h followed by the addition of triethylamine (50.4 mL, 0.362 mole) and water (12 mL). The solution was stirred at ambient temperature overnight, evaporated and partitioned between ethyl acetate and water. The aqueous layer was extracted twice with ethyl acetate, combined, washed with brine, dried ($Na_2SO_4$), filtered and evaporated. Triphenylphosphine oxide which was precipitated from the crude product with ether and hexane was separated by filtration. The filtrate was concentrated and the residue was purified by filtration through a short column of silica gel eluting with ethyl acetate/methanol to give 31 (55.2 g, 81%) as a yellow oil.

Example 11

Compound 32: To a solution of 31 (55 g, 0.242 mole) in N,N-dimethylformamide (560 mL) was added sodium azide (78.7 g, 1.21 mole) and ammonium chloride (25.9 g, 0.484 mole). The mixture was stirred at 65° C. for 18 h, cooled, diluted with dicholomethane (500 mL) and filtered. The filtrate was concentrated and filtered through a pad of silica gel eluting with ethyl acetate/hexane (1:1) to give 32 (59.2 g, 91%) as a yellow oil.

Example 12

Compound 1: A mixture of 32 (59.2 g, 0.22 mole) and HCl/ethanol (6.2% w/w, 520 mL) was stirred at ambient temperature for 8 h. Solvents were evaporated and the residue was precipitated from ether to give 1 (50.2 g, 87%) as a brown solid.

Example 13

Compound 2: To a solution of alcohol 1 (2.0 g, 7.61 mmol) in dry pyridine (25 mL) at ambient temperature was added catalytic 4-dimethylamino pyridine (ca. 50 mg) and acetic anhydride (3.0 mL, 31.8 mmol). The reaction mixture was stirred for 24 h at ambient temperature, concentrated and partitioned between ethyl acetate and water. The organic layer was separated and sequentially washed with 1 N HCl, water, satd. NaHCO$_3$, brine and dried (MgSO$_4$). Concentration in vacuo gave a solid which was recrystallized from ethyl acetate/hexane to give 1.9 g (81%) of 2 as an off-white solid. $^1$H NMR (CDCl$_3$): δ6.65 (t, J=2.1 Hz, 1H); 5.70–5.66 (m, 2H); 4.23 (q, J=7.2 Hz, 2H); 4.15–4.04 (m, 1H); 3.82–3.74 (m, 1H); 3.00–2.91 (m, 1H); 2.46–2.34 (m, 1H); 2.11 (s, 3H); 2.03 (s, 3H); 1.31 (t, J=7.2 Hz, 3H).

Example 14

Compound 3c: To a solution of 2 (360 mg, 1.16 mmol) in dry THF (4.8 mL) was added Tetrakis(triphenylphosphine)palladium(0) (67.0 mg, 0.058 mmol) and N-methyl(1-ethyl propyl)amine (294 mg, 2.90 mmol). The mixture was refluxed for 4 h, concentrated and purified by chromatography eluting with ethyl acetate/hexane (3:7) to give 3c (153 mg, 38%) as an orange oil.

Example 15

Compound 4c: To a solution of azide 3c (153 mg, 0.435 mmol) in THF (6.5 mL) was added triphenylphosphine (172 mg, 0.656 mmol) and water (783 μL). The solution was heated at 50° C. for 10 h and concentrated. The residue was diluted with ethyl acetate, dried (Na$_2$SO$_4$), filtered and evaporated. Purification of the residue by chromatography eluting with ethyl acetate/methanol (7:3) gave 4c (75 mg, 53%). HRMS (FAB) calcd for C$_{17}$H$_{32}$N$_3$O$_3$ (MH$^+$) 326.2443, found 326.2443.

Example 16

Compound 5c: To a solution of 4c (59 mg, 0.181 mmol) in THF (1.48 mL) was added 0.974 N potassium hydroxide (186 μL, 0.181 mmol). The reaction mixture was stirred at ambient temperature for 24 h. Solvents were evaporated and the residue was purified by C$_{18}$ chromatography eluting with water. Fractions containing the desired product were pooled and lyophilized to afford 5c (50 mg, 83%) as an off-white solid. $^1$H NMR (D$_2$O) δ6.55 (s, 1H), 3.73 (t, J=11 Hz, 1H), 3.55 (m, 1H), 2.82 (m, 1H), 2.62 (m, 1H), 2.36 (m, 1H), 2.19 (s, 3H), 2.06 (m, 1H), 2.03 (s, 3H), 1.36–1.48 (m, 4H), 0.86 (m, 6H); HRMS (FAB) calcd for C$_{15}$H$_{27}$KN$_3$O$_3$ (MH$^+$) 336.1689, found 336.1698.

Example 17

Compounds 5a, 5b, 5d, 5e, 5f, 5g, 5h, 5i, 5j, 5k, 5l, 5m: Prepared from 2 by a method similar to that described for 5c.

Example 18

Compound 6: To a solution of 2 (1.02 g, 3.28 mmol) in THF (49 mL) was added triphenylphosphine (1.29 g, 4.9 mmol) and water (5.9 mL). The mixture was heated at 50° C. for 10 h. Solvents were evaporated and the residue was diluted with ethyl acetate, dried (Na$_2$SO$_4$), filtered and evaporated. The residue was purified by chromatography eluting with ethyl acetate/methanol (4:1) to give 6. HRMS (FAB) calcd for C$_{13}$H$_{21}$N$_2$O$_5$ (MH$^+$) 285.1450, found 285.1452.

Example 19

Compound 7: To a solution of 6 (920 mg, 3.24 mmol) in dry acetonitrile (19 mL) was added Di-tert-butyl dicarbonate (884 mg, 4.05 mmol). The mixture was stirred at ambient temperature for 2.5 h and concentrated to give a residue which was precipitated from ethyl acetate and hexane to give 7 (1.25 g, 100%) as a colorless solid. HRMS (FAB) calcd for C$_{18}$H$_{29}$N$_2$O$_7$ (MH$^+$) 385.1974, found 385.1981.

Example 20

Compound 8: To a solution of 7 (1.0 g, 2.60 mmol) in THF (6.6 mL) and water (2.3 mL) was added Tetrakis(triphenylphosphine)palladium(0) (91 mg, 0.079 mmol) and sodium azide (190 mg, 2.92 mmol). The solution was heated at 75° C. for 3 h and then extracted with ethyl ether. The combined organic extracts were washed with 2N HCl, saturated sodium bicarbonate, brine, dried (MgSO$_4$), filtered and evaporated. The residue was purified by chromatography eluting with ethyl acetate/hexane (4:6) to give 8 (610 mg, 64%) as an off white solid. HRMS (FAB) calcd for C$_{16}$H$_{26}$N$_5$O$_5$ (MH$^+$) 368.1934, found 368.1927.

Example 21

Compound 9: To a solution of azide 8 (650 mg, 1.77 mmol) in THF (26 mL) was added triphenylphosphine (697 mg, 2.66 mmol) and water (3.25 mL). The solution was heated at 50° C. for 10 h. Solvents were evaporated and the residue diluted with ethyl acetate, dried (Na$_2$SO$_4$), filtered and evaporated. The residue was purified by chromatography eluting with ethyl acetate/methanol (4:1) to give 9 (551 mg, 91%). HRMS (FAB) calcd for C$_{16}$H$_{28}$N$_3$O$_5$ (MH$^+$) 342.2029, found 342.2031.

Example 22

Compound 10a: To a solution of 9 (200 mg, 0.586 mmol) in anhydrous methanol (1.7 mL) was added 3-pentanone (119 μL, 1.17 mmol) followed by the addition of a solution of NaCNBH$_3$ (74 mg, 1.17 mmol) and ZnCl$_2$ (80 mg, 0.587 mmol) in anhydrous methanol (1.7 mL). The mixture was stirred at ambient temperature for 26 h and quenched with saturated ammonium chloride. Volatiles were removed under reduced pressure followed by extraction with ethyl ether. The combined organic extracts were washed with saturated sodium bicarbonate, brine, dried (Na$_2$SO$_4$), filtered through a thin pad of silica gel and evaporated to give 10a (168 mg, 70%) as a colorless solid. HRMS (FAB) calcd for C$_{21}$H$_{38}$N$_3$O$_5$ (MH$^+$) 412.2811, found 412.2801.

Example 23

Compound 11a: Compound 10a (161 mg, 0.391 mmol) was dissolved in trifluoroacetic acid (10% in CH$_2$Cl$_2$, 8.8 mL). The mixture was stirred at ambient temperature for 2.5 h and evaporated. The residue was dissolved in ethyl acetate and washed with saturated sodium bicarbonate, dried (Na$_2$SO$_4$), filtered and evaporated. The residue was purified by chromatography eluting with ethyl acetate/methanol (6:4) to give 11a (107 mg, 86%). HRMS (FAB) calcd for C$_{16}$H$_{30}$N$_3$O$_3$(MH$^+$) 312.2287, found 312.2290.

Example 24

Compound 12a: To a solution of 11a (50 mg, 0.161 mmol) in THF (1.32 mL) was added 0.974 N potassium hydroxide (165 μL, 0.161 mmol). The reaction mixture was stirred at ambient temperature for 21 h. Solvents were evaporated and the residue was purified by C$_{18}$ chromatogrphy eluting with water. Fractions containing the desired product were pooled and lyopholized to afford 12a (40 mg, 77%) as an off-white solid. $^1$H NMR (D$_2$O) δ6.40 (s, 1H), 3.56 (t, J=11 Hz, 1H), 3.38 (m, 1H), 2.87 (m, 1H), 2.64 (m, 1H), 2.54 (m, 1H), 2.09 (m, 1H), 2.06 (s, 3H), 1.40 (m, 4H), 0.82 (m, 6H); HRMS (FAB) calcd for C$_{14}$H$_{25}$KN$_3$O$_3$ (MH$^+$) 322.1533, found 322.1532.

Example 25

Compound 12b: The title compound was prepared in 33% yield from amine 9 by a method similar to that described for compound 12a. $^1$H NMR (D$_2$O) δ6.35 (s, 1H), 3.69 (t, J=11 Hz, 1H), 3.38 (m, 1H), 2.84 (m, 1H), 2.64 (m, 1H), 2.42–2.55 (m, 2H), 2.08 (m, 1H), 2.04 (s, 3H), 1.42 (m, 2H), 0.85 (m, 3H); C$_{12}$H$_{20}$KN$_3$O$_3$ (MH$^+$) 294.1220, found 294.1221.

Example 26

Enzyme Inhibition: Using the methods of screening in vitro activity described above, the following activities were observed:

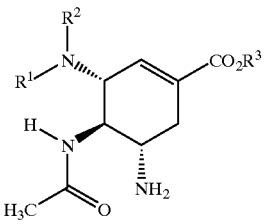

| compound | R$_1$ | R$_2$ | Neuraminidase IC$_{50}$ (nM) | |
|---|---|---|---|---|
| | | | Flu A | Flu B |
| 12a | H | CH(CH$_2$CH$_3$)$_2$ | 11.5 | 100 |
| 12b | H | CH$_2$CH$_2$CH$_3$ | 200 | 240 |
| 5a | CH$_3$ | CH$_2$CH$_2$CH$_3$ | 65 | 65 |
| 5b | CH$_3$ | CH$_2$CH$_2$CH$_2$CH$_3$ | 180 | ND |
| 5c | CH$_3$ | CH(CH$_2$CH$_3$)$_2$ | 6 | 60 |
| 5d | CH$_3$ | CH$_2$CH(CH$_2$CH$_3$)$_2$ | 120 | ND |
| 5e | CH$_3$ | CH$_2$CH$_2$C$_6$H$_5$ | 100 | 565 |
| 5f | CH$_3$ | C$_6$H$_{11}$ | 200 | >1000 |
| 5g | CH$_2$CH$_3$ | CH$_2$CH$_2$CH$_3$ | 90 | ND |
| 5h | CH$_2$CH$_3$ | CH$_2$CH$_2$CH$_2$CH$_3$ | 85 | 175 |
| 5i | CH$_2$CH$_2$CH$_3$ | CH$_2$CH$_2$CH$_3$ | 12 | 60 |
| 5j | CH$_2$CH$_2$CH$_3$ | CH$_2$C$_3$H$_5$ | 50 | ND |
| 5k | —CH$_2$CH$_2$CH$_2$CH$_2$— | | 400 | ND |
| 5l | —CH$_2$CH$_2$CH$_2$CH$_2$CH$_2$— | | 30 | 3 |
| 5m | —CH$_2$CH$_2$OCH$_2$CH$_2$— | | 200 | 30 |

ND means No Data.

All literature and patent citations above are hereby expressly incorporated by reference in their entirety at the locations of their citation. Specifically cited sections or pages of the above cited works are incorporated by reference with specificity. The invention has been described in detail sufficient to allow one of ordinary skill in the art to make and use the subject matter of the following claims. It is apparent that certain modifications of the methods and compositions of the following claims can be made within the scope and spirit of the invention.

What is claimed is:

1. A compound of the formula (I):

wherein:

R$^1$ is H, R$^2$ is —CH(CH$_2$CH$_3$)$_2$ and R$^3$ is H;

R is H, R$^2$ is —CH(CH$_2$CH$_3$)$_2$ and R$^3$ is —CH$_2$CH$_3$;

R$^1$ is H, R$^2$ is —CH$_2$CH$_2$CH$_3$ and R$^3$ is H;

R$^1$ is H, R$^2$ is —CH$_2$CH$_2$CH$_3$ and R$^3$ is —CH$_2$CH$_3$;

R$^1$ is —CH$_3$, R$^2$ is —CH$_2$CH$_2$CH$_3$ and R$^3$ is H;

R$^1$ is —CH$_3$, R$^2$ is —CH$_2$CH$_2$CH$_3$ and R$^3$ is —CH$_2$CH$_3$;

R$^1$ is —CH$_3$, R$^2$ is —CH$_2$CH$_2$CH$_2$CH$_3$ and R$^3$ is H;

R$^1$ is —CH$_3$, R$^2$ is —CH$_2$CH$_2$CH$_2$CH$_3$ and R$^3$ is —CH$_2$CH$_3$;

R$^1$ is —CH$_3$, R$^2$ is —CH(CH$_2$CH$_3$)$_2$ and R$^3$ is H;

R$^1$ is —CH$_3$, R$^2$ is —CH(CH$_2$CH$_3$)$_2$ and R$^3$ is —CH$_2$CH$_3$;

R$^1$ is —CH$_3$, R$^2$ is —CH$_2$CH(CH$_2$CH$_3$)$_2$ and R$^3$ is H;

R$^1$ is —CH$_3$, R$^2$ is —CH$_2$CH(CH$_2$CH$_3$)$_2$ and R$^3$ is —CH$_2$CH$_3$;

R$^1$ is —CH$_3$, R$^2$ is —CH$_2$CH$_2$Ph and R$^3$ is H;

R$^1$ is —CH$_3$, R$^2$ is —CH$_2$CH$_2$Ph and R$^3$ is —CH$_2$CH$_3$;

R$^1$ is —CH$_3$, R$^2$ is -(cyclohexyl) and R$^3$ is H;

R$^1$ is —CH$_3$, R$^2$ is -(cyclohexyl) and R$^3$ is —CH$_2$CH$_3$;

R$^1$ is —CH$_2$CH$_3$, R$^2$ is —CH$_2$CH$_2$CH$_3$ and R$^3$ is H;

R$^1$ is —CH$_2$CH$_3$, R$^2$ is —CH$_2$CH$_2$CH$_3$ and R$^3$ is —CH$_2$CH$_3$;

R$^1$ is —CH$_2$CH$_3$, R$^2$ is —CH$_2$CH$_2$CH$_2$CH$_3$ and R$^3$ is H;

R$^1$ is —CH$_2$CH$_3$, R$^2$ is —CH$_2$CH$_2$CH$_2$CH$_3$ and R$^3$ is —CH$_2$CH$_3$;

R$^1$ is —CH$_2$CH$_2$CH$_3$, R$^2$ is —CH$_2$CH$_2$CH$_3$ and R$^3$ is H;

R$^1$ is —CH$_2$CH$_2$CH$_3$, R$^2$ is —CH$_2$CH$_2$CH$_3$ and R$^3$ is —CH$_2$CH$_3$;

R$^1$ is —CH$_2$CH$_2$CH$_3$, R$^2$ is —CH$_2$(cyclopropyl) and R$^3$ is H;

R$^1$ is —CH$_2$CH$_2$CH$_3$, R$^2$ is —CH$_2$(cyclopropyl) and R$^3$ is —CH$_2$CH$_3$;

R$^1$ and R$^2$ are taken together to form —CH$_2$CH$_2$CH$_2$CH$_2$— and R$^3$ is H;

R$^1$ and R$^2$ are taken together to form —CH$_2$CH$_2$CH$_2$CH$_2$— and R$^3$ is —CH$_2$CH$_3$;

R$^1$ and R$^2$ are taken together to form —CH$_2$CH$_2$CH$_2$CH$_2$CH$_2$— and R$^3$ is H;

R$^1$ and R$^2$ are taken together to form —CH$_2$CH$_2$CH$_2$CH$_2$CH$_2$— and R$^3$ is —CH$_2$CH$_3$;

R¹ and R² are taken together to form —CH₂CH₂OCH₂CH₂— and R³ is H; or

R¹ and R² are taken together to form —CH₂CH₂OCH₂CH₂— and R³ is —CH₂CH₃;

and salts, solvates and resolved enantiomers thereof.

2. The compound of claim 1 wherein R¹ is H, R² is —CH(CH₂CH₃)₂ and R³ is H.

3. The compound of claim 1 wherein R¹ is H, R² is —CH(CH₂CH₃)₂ and R³ is —CH₂CH₃.

4. The compound of claim 1 wherein R¹ is H, R² is —CH₂CH₂CH₃ and R³ is H.

5. The compound of claim 1 wherein R¹ is H, R² is —CH₂CH₂CH₃ and R³ is —CH₂CH₃.

6. The compound of claim 1 wherein R¹ is —CH₃, R² is —CH₂CH₂CH₃ and R³ is H.

7. The compound of claim 1 wherein R¹ is —CH₃, R² is —CH₂CH₂CH₃ and R³ is —CH₂CH₃.

8. The compound of claim 1 wherein R¹ is —CH₃, R² is —CH₂CH₂CH₂CH₃ and R³ is H.

9. The compound of claim 1 wherein R¹ is —CH₃, R² is —CH₂CH₂CH₂CH₃ and R³ is —CH₂CH₃.

10. The compound of claim 1 wherein R¹ is —CH₃, R² is —CH(CH₂CH₃)₂ and R³ is H.

11. The compound of claim 1 wherein R¹ is —CH₃, R² is —CH(CH₂CH₃)₂ and R³ is —CH₂CH₃.

12. The compound of claim 1 wherein R¹ is —CH₃, R² is —CH₂CH(CH₂CH₃)₂ and R³ is H.

13. The compound of claim 1 wherein R¹ is —CH₃, R² is —CH₂CH(CH₂CH₃)₂ and R³ is —CH₂CH₃.

14. The compound of claim 1 wherein R¹ is —CH₃, R² is —CH₂CH₂Ph and R³ is H.

15. The compound of claim 1 wherein R¹ is —CH₃, R² is —CH₂CH₂Ph and R³ is —CH₂CH₃.

16. The compound of claim 1 wherein R¹ is —CH₃, R² is -(cyclohexyl) and R³ is H.

17. The compound of claim 1 wherein R¹ is —CH₃, R² is -(cyclohexyl) and R³ is —CH₂CH₃.

18. The compound of claim 1 wherein R¹ is —CH₂CH₃, R² is —CH₂CH₂CH₃ and R³ is H.

19. The compound of claim 1 wherein R¹ is —CH₂CH₃, R² is —CH₂CH₂CH₃ and R³ is —CH₂CH₃.

20. The compound of claim 1 wherein R¹ is —CH₂CH₃, R² is —CH₂CH₂CH₂CH₃ and R³ is H.

21. The compound of claim 1 wherein R¹ is —CH₂CH₃, R² is —CH₂CH₂CH₂CH₃ and R³ is —CH₂CH₃.

22. The compound of claim 1 wherein R¹ is —CH₂CH₂CH₃, R² is —CH₂CH₂CH₃ and R³ is H.

23. The compound of claim 1 wherein R¹ is —CH₂CH₂CH₃, R² is —CH₂CH₂CH₃ and R³ is —CH₂CH₃.

24. The compound of claim 1 wherein R¹ is —CH₂CH₂CH₃, R² is —CH₂(cyclopropyl) and R³ is H.

25. The compound of claim 1 wherein R¹ is —CH₂CH₂CH₃, R² is —CH₂(cyclopropyl) and R³ is —CH₂CH₃.

26. The compound of claim 1 wherein R¹ and R² are taken together to form —CH₂CH₂CH₂CH₂— and R³ is H.

27. The compound of claim 1 wherein R¹ and R² are taken together to form —CH₂CH₂CH₂CH₂— and R³ is —CH₂CH₃.

28. The compound of claim 1 wherein R¹ and R² are taken together to form —CH₂CH₂CH₂CH₂CH₂— and R³ is H.

29. The compound of claim 1 wherein R¹ and R² are taken together to form —CH₂CH₂CH₂CH₂CH₂— and R³ is —CH₂CH₃.

30. The compound of claim 1 wherein R¹ and R² are taken together to form —CH₂CH₂OCH₂CH₂— and R³ is H.

31. The compound of claim 1 wherein R¹ and R² are taken together to form —CH₂CH₂OCH₂CH₂— and R³ is —CH₂CH₃.

32. A compound of claim 1 further comprising a pharmaceutically-acceptable carrier.

33. A method of inhibiting the activity of neuraminidase comprising the step of contacting a sample suspected of containing neuraminidase with a compound of claim 1.

34. The method of claim 33 wherein the neuraminidase is influenza neuraminidase in vivo.

35. A method for the treatment or prophylaxis of influenza infection in a host comprising administering to the host a therapeutically effective amount of a compound of claim 1.

36. The method of claim 35 wherein the compound further comprises a pharmaceutically-acceptable carrier.

* * * * *